US011538574B2

(12) United States Patent
Holladay et al.

(10) Patent No.: US 11,538,574 B2
(45) Date of Patent: Dec. 27, 2022

(54) REGISTRATION OF SPATIAL TRACKING SYSTEM WITH AUGMENTED REALITY DISPLAY

(71) Applicant: CENTERLINE BIOMEDICAL, INC., Cleveland, OH (US)

(72) Inventors: Matthew Holladay, Cleveland, OH (US); Vikash Goel, Cleveland, OH (US)

(73) Assignee: CENTERLINE BIOMEDICAL, INC., Cleveland, OH (US)

( * ) Notice: Subject to any disclaimer, the term of this patent is extended or adjusted under 35 U.S.C. 154(b) by 395 days.

(21) Appl. No.: 16/840,915

(22) Filed: Apr. 6, 2020

(65) Prior Publication Data

US 2020/0321099 A1    Oct. 8, 2020

Related U.S. Application Data

(60) Provisional application No. 62/838,027, filed on Apr. 24, 2019, provisional application No. 62/829,394, filed on Apr. 4, 2019.

(51) Int. Cl.
*G06K 9/00*    (2022.01)
*A61B 5/05*    (2021.01)
(Continued)

(52) U.S. Cl.
CPC .......... *G16H 30/20* (2018.01); *G02B 27/017* (2013.01); *G06T 7/0012* (2013.01); *G06T 7/97* (2017.01); *G06T 19/006* (2013.01)

(58) Field of Classification Search
CPC .................................. G06K 9/00; A61B 5/05
(Continued)

(56) References Cited

U.S. PATENT DOCUMENTS 6,533,455 B2    3/2003  Graumann et al.
7,010,095 B2    3/2006  Mitschke et al.
(Continued)

FOREIGN PATENT DOCUMENTS

EP    1421913 A1    5/2004
JP    2007185278 A    7/2007
(Continued)

OTHER PUBLICATIONS

Applicant: Centerline Biomedical, Inc.; International PCT Application No. PCT/US2020/026868; Filed: Apr. 6, 2020; PCT International Search Report and PCT Written Opinion; Authorized Officer: Yang Jeong Rok, dated Jul. 13, 2020; 13 pgs.
(Continued)

*Primary Examiner* — Seyed H Azarian
(74) *Attorney, Agent, or Firm* — Tarolli, Sundheim, Covell & Tummino LLP

(57)  ABSTRACT

An example method may include acquiring images from cameras, each having a known position and orientation with respect to a spatial coordinate system of an augmented reality (AR) device. The acquired images may include portions of a multi-modal marker device that includes at least one tracking sensor having a three-dimensional position that is detectable in a coordinate system of a tracking system. A three-dimensional position is estimated for the portions of the multi-modal marker device with respect to the spatial coordinate system of the AR device based on each of the respective acquired images and the known position and orientation of the cameras with respect to the spatial coordinate system of the AR device. The method also includes computing an affine transform configured to register the coordinate system of the tracking system with a visual space of a display that is in the spatial coordinate system of the AR device.

25 Claims, 8 Drawing Sheets

(51) Int. Cl.
*G16H 30/20* (2018.01)
*G06T 19/00* (2011.01)
*G02B 27/01* (2006.01)
*G06T 7/00* (2017.01)

(58) Field of Classification Search
USPC ....... 382/100, 103, 107, 128–133, 154, 162, 382/168, 173, 181, 199, 224, 254, 260, 382/274, 276, 285–291, 305; 378/4, 21; 600/407, 414
See application file for complete search history.

(56) References Cited

U.S. PATENT DOCUMENTS

| | | | |
|---|---|---|---|
| 7,556,428 B2 | 7/2009 | Sukovic et al. | |
| 7,671,887 B2 | 3/2010 | Pescatore et al. | |
| 7,824,328 B2 | 11/2010 | Gattani et al. | |
| 3,060,185 A1 | 11/2011 | Hunter et al. | |
| 8,213,693 B1 | 7/2012 | Li | |
| 8,224,632 B2 | 7/2012 | Whirley et al. | |
| 8,238,625 B2 | 8/2012 | Strommer et al. | |
| 8,248,413 B2 | 8/2012 | Gattani et al. | |
| 8,301,226 B2 | 10/2012 | Csavoy et al. | |
| 8,315,355 B2 | 11/2012 | Mohamed | |
| 8,467,853 B2 | 6/2013 | Hunter et al. | |
| 9,240,043 B2 | 1/2016 | Carrell et al. | |
| 10,176,582 B2 | 1/2019 | Carrell et al. | |
| 10,511,822 B2* | 12/2019 | Casas | G06F 3/0304 |
| 10,650,513 B2 | 5/2020 | Penney et al. | |
| 2003/0011624 A1 | 1/2003 | Ellis | |
| 2007/0055128 A1 | 3/2007 | Glossop | |
| 2008/0020362 A1 | 1/2008 | Cotin et al. | |
| 2009/0227861 A1 | 9/2009 | Ganatra et al. | |
| 2010/0210938 A1 | 8/2010 | Verard | |
| 2010/0312094 A1 | 12/2010 | Guttman et al. | |
| 2011/0026793 A1 | 2/2011 | Goel | |
| 2011/0054300 A1 | 3/2011 | Yamamoto et al. | |
| 2011/0166446 A1 | 7/2011 | Whitmore, III et al. | |
| 2011/0295109 A1 | 12/2011 | Lavallee et al. | |
| 2013/0079628 A1 | 3/2013 | Groszmann | |
| 2013/0237811 A1* | 9/2013 | Mihailescu | A61B 8/5269 600/407 |
| 2013/0245461 A1 | 9/2013 | Maier-Hein et al. | |
| 2014/0276002 A1 | 9/2014 | West et al. | |
| 2015/0138186 A1 | 5/2015 | Carrell et al. | |
| 2017/0027651 A1* | 2/2017 | Esterberg | G06F 3/011 |
| 2017/0178324 A1 | 6/2017 | Saget et al. | |
| 2017/0345219 A1 | 11/2017 | Holz | |
| 2018/0040147 A1 | 2/2018 | Alhrishy et al. | |
| 2018/0303377 A1 | 10/2018 | West et al. | |
| 2019/0304108 A1 | 10/2019 | Carrell et al. | |
| 2019/0336004 A1* | 11/2019 | Mihailescu | A61B 90/361 |
| 2020/0275988 A1* | 9/2020 | Johnson | A61B 90/37 |
| 2021/0212772 A1* | 7/2021 | Yang | A61B 90/30 |

FOREIGN PATENT DOCUMENTS

| | | |
|---|---|---|
| JP | 2007209531 A | 8/2007 |
| JP | 2008061858 A | 3/2008 |
| JP | 2008136850 A | 6/2008 |
| JP | 2009072317 A | 4/2009 |
| JP | 2012147858 A | 8/2012 |
| JP | 2012529352 A | 11/2012 |
| JP | 2013171522 A | 9/2013 |
| JP | 2017153827 A | 9/2017 |
| KR | 10-2017-0021189 A | 2/2017 |
| WO | 2005119578 A2 | 12/2005 |
| WO | 2008/035271 A2 | 3/2008 |
| WO | 2010/074986 A1 | 7/2010 |
| WO | 2010086374 A1 | 8/2010 |
| WO | 2012127353 A1 | 9/2012 |
| WO | 2012143290 A1 | 10/2012 |

OTHER PUBLICATIONS

Mohapatra, et al., "Radiation Exposure to Operating Room Personnel and Patients During Endovascular Procedures", Journal of Vascular Surgery, 2013, pp. 1-8.
ArUco Marker Detection (aruco module); Oopen CV—Open Source Computer Visionhttps://docs.opencv.org/master/d9/d6d/tutorial_table_of_content_aruco.html; Aug. 14, 2020; 1 pg.
HoloLens research Mode; https://docs.microsoft.com/en-us/windows/mixed-reality/research-mode; Aug. 14, 2020; 5 pgs.
https://github.com/Microsoft/HoloLensForCV; Aug. 14, 2020; 3 pgs.
Applicant: Centerline Biomedical, Inc.; "Registration of Spatial Tracking System with Augmented Reality Display" Canadian Office Action dated Oct. 3, 2022; 4 pgs.
Tomonori Hamaji et al., "Proposal of seamless optical/video see-through HMD and AR information Optimization of Information Presentation Control, Proceedings of the 34th Fuzzy System Symposium"; (FSS2018 Nagoya University), Japan Society for Intelligent Information Fuzzy, Sep. 3, 2018, p. 750-754 (Documents showing well-known technology).
Applicant: Centerline Biomedical, Inc.; Japanese Office Action dated Oct. 11, 2022; 3 pgs.

* cited by examiner

REGISTRATION OF SPATIAL TRACKING SYSTEM WITH AUGMENTED REALITY DISPLAY

CROSS-REFERENCE TO RELATED APPLICATIONS

This application claims priority from U.S. provisional application Nos. 62/838,027, filed Apr. 24, 2019, and entitled REGISTRATION OF SPATIAL TRACKING SYSTEM WITH AUGMENTED REALITY DISPLAY, and 62/829,394, filed Apr. 4, 2019, and entitled SPATIAL REGISTRATION OF TRACKING SYSTEM WITH AN IMAGE USING TWO-DIMENSIONAL IMAGE PROJECTIONS, each of which is incorporated herein by reference in its entirety.

TECHNICAL FIELD

This disclosure relates to systems and methods for registering a tracking system with an augmented reality system.

BACKGROUND

Augmented (or mixed) reality is an interactive experience of a real-world environment where the objects that reside in the real-world are "augmented" by computer-generated perceptual information, such as by overlaying constructive or destructive sensory information. One example of constructive sensory information example is use of an augmented reality headset to overlay computer-generated graphics on a real physical view of an environment such that it is perceived as an immersive aspect of the real environment. Since the headset is fixed to a user, however, the computer-generated graphics need to be properly registered on-the-fly into the real physical view of the environment. This becomes more complicated when the registered graphics being registered are not representative of objects visible in the environment.

SUMMARY

This disclosure relates to systems and methods for registering a tracking system with an augmented reality system.

As an example, a method includes acquiring images from cameras, each having a known position and orientation with respect to a spatial coordinate system of an augmented reality device. The acquired images may include predetermined portions of a multi-modal marker device that have a fixed known spatial position with respect to at least one tracking sensor of the multi-modal marker device. The at least one tracking sensor having a three-dimensional position that is detectable in a coordinate system of a tracking system. The method also includes estimating a three-dimensional position for the predetermined portions of the multi-modal marker device with respect to the spatial coordinate system of the augmented reality device based on each of the respective acquired images and the known position and orientation of the cameras with respect to the spatial coordinate system of the augmented reality device. The method also includes computing an affine transform configured to register the coordinate system of the tracking system with a visual space of a display that is in the spatial coordinate system of the augmented reality device based on the estimated three-dimensional position for respective predetermined portions of the multi-modal marker device and the known spatial position of the predetermined portions of the multi-modal marker device relative to the at least one tracking sensor.

As another example, a system includes an augmented reality device that includes cameras to acquire images for respective fields of view. One or more non-transitory computer-readable media is configured to store data and instructions executable by a processor. The data includes augmented reality image data for images acquired by the cameras, each camera having a known position and orientation with respect to a spatial coordinate system of the augmented reality device. The augmented reality image data may include predetermined portions of a multi-modal marker device having a fixed known spatial position with respect to at least one tracking sensor of the multi-modal marker device, and the at least one tracking sensor has a three-dimensional position that is detectable in a coordinate system of a tracking system. The instructions include code to generate a three-dimensional position for the predetermined portions of the multi-modal marker device with respect to the spatial coordinate system of the augmented reality device based on the augmented reality image data that is acquired and the known position and orientation of the cameras with respect to the spatial coordinate system of the augmented reality device. The instructions further include code to compute an affine transform for registering the coordinate system of the tracking system with a visual space of a display that is in the spatial coordinate system of the augmented reality device based on the three-dimensional position for the respective predetermined portions of the multi-modal marker device and the known spatial position and orientation of the predetermined portions of the multi-modal marker device relative to the at least one tracking sensor.

DETAILED DESCRIPTION

Figure 1:
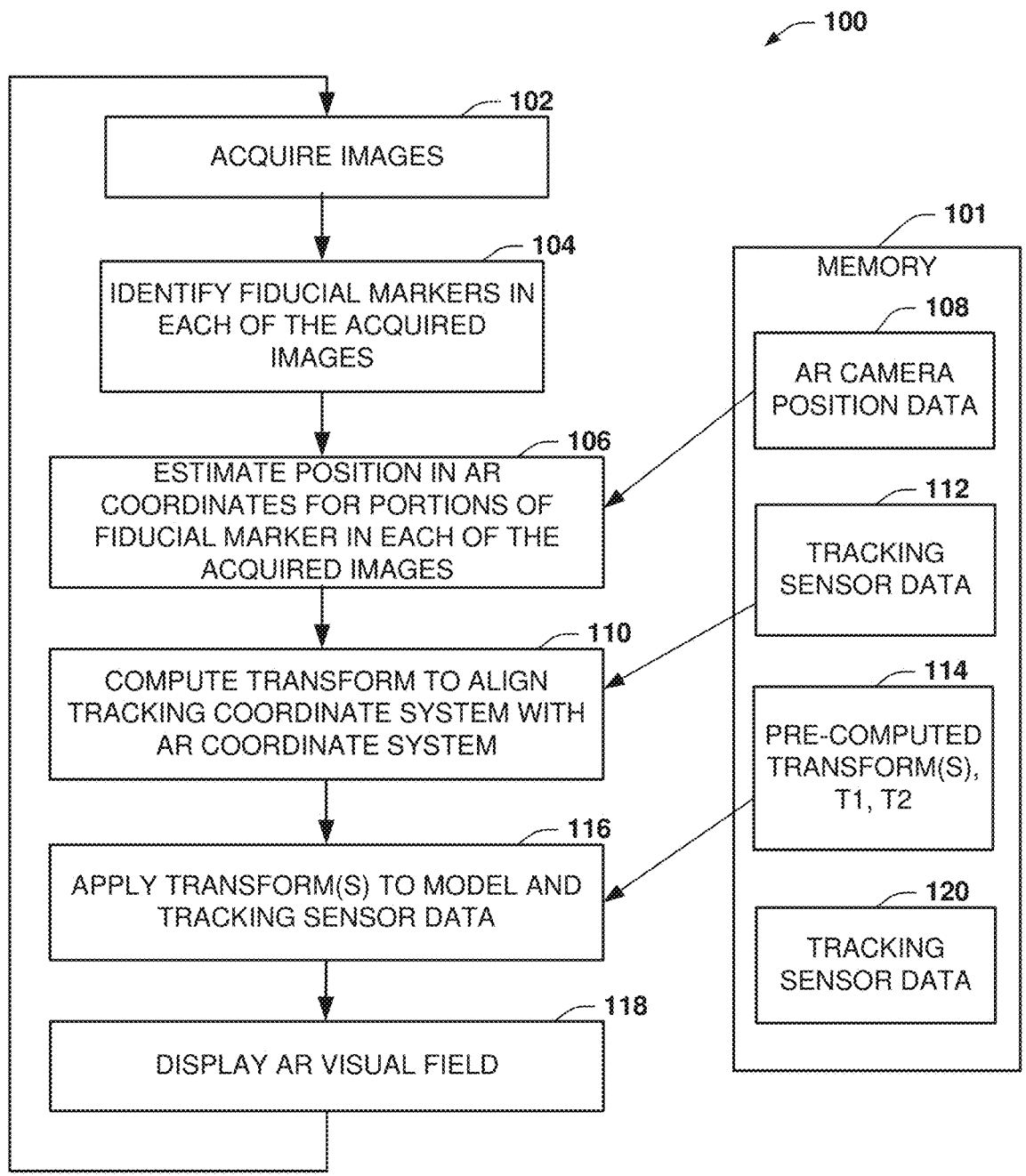
FIG. 1 is a flow diagram depicting an example of a method to register sensors of a tracking system into a spatial coordinate system of an augmented reality display.

This disclosure relates generally to methods and systems for registering a tracking system and a set of one or more models with an augmented reality (AR) visual field that is rendered on an AR display device, such as a head-mounted display. The method utilizes a marker device (e.g., a multi-modal marker) that includes fiducial markers detectable by more than one modality. For example, the marker device includes a first fiducial marker to provide a pattern that is visible in an image generated by set of cameras having a fixed position with respect to a visualization space (e.g., the AR visual field) and another set of one or more markers detectable by a three-dimensional spatial tracking system.

As an example, an arrangement of two or more cameras (e.g., digital grayscale cameras) are mounted as forward-facing cameras spaced apart from each other along a frame of the AR device. The cameras are thus configured to provide two-dimensional images for an overlapping field of view. In this way, the field of view of the cameras includes the visual field of the AR device and can include one or more fiducial markers of the multi-modal marker device. In addition to one or more fiducial markers visible to the spectrum of the camera, which may be invisible to the human eye, the marker device also includes one or more second fiducial markers (e.g., one or more tracking sensors) detectable by a three-dimensional spatial tracking system. Each second fiducial marker is arranged in a predetermined spatial position and orientation with respect to the first fiducial markers that are discernable in the respective images (e.g., real time images) acquired by the cameras.

As a further example, each of the cameras acquires images that include a field of view that includes a marker pattern corresponding to the first fiducial marker of the marker device. Each of the images is processed to locate and identify predetermined portions of the pattern (e.g., corners of a rectangular printed mark) in each respective image. Using the known (e.g., fixed) position of each camera with respect to the AR device, the identified portions (e.g., points or regions) of the marker pattern are converted to corresponding three-dimensional locations in a three-dimensional spatial coordinate system of the AR system, namely, the AR field of view.

The position and orientation for one or more tracking sensors with respect to the fiducial marker(s) are further stored as tracking position data in memory. Additionally, one or more affine transforms can be precomputed to align the tracking sensor(s) with a coordinate system is also stored in memory (e.g., as a tracking-to-model system transform). In an example, the precomputed transform is a set of one or more affine transforms that is pre-computed to register a tracking coordinate system with a prior three-dimensional (3D) image scan (e.g., a pre-procedure scan). The prior 3D image scan may be a high-resolution imaging technique, such as computed tomography (CT) scan, magnetic resonance imaging (MRI), which may be performed hours, days or even weeks in advance of a procedure. One or more models may be derived from the prior 3D image scan, such as a centerline model and/or mesh model of a tubular anatomic structure, and thus be spatially registered in the coordinate system of the prior 3D image. As disclosed herein, the precomputed affine transform(s) can be computed to register the position and orientation of each tracking sensor in a common coordinate system with the prior 3D image.

Another affine transform (also referred to herein as an AR alignment transform or zero transform matrix) is computed to align a coordinate system of the tracking system with the AR coordinate system. For example, the AR alignment transform is determined based on the tracking position data, AR image data and a tracking sensor transform. The tracking sensor transform may define a predetermined spatial relationship between a tracking sensor and one or fiducials that are integrated into and have fixed spatial offsets in a multi-modal marker device and enables determining predetermined spatial position portions of the marker in the coordinate space of the tracking system. Thus, the AR alignment transform enables the systems and methods to register position and orientation information of each tracking sensor(s), as provided by the tracking system, and the coordinate system of the AR system modality. Additional transforms disclosed herein may further be utilized to transform from other spatial domains into the AR coordinate system for rendering in an AR display concurrently. As disclosed herein, the AR display device and tracking sensors may move relative to a patient's body and the system can continuously (e.g., in real time) recompute the transforms based on such AR image data and tracking sensor data that varies over time.

FIG. 1 is a flow diagram depicting an example of a method 100 for registering a three-dimensional coordinate system with a coordinate system of an AR visual display of an AR device. In an example, the method 100 is a set of machine-readable instructions that are executable by a processor device to perform the method based on data stored in memory 101. By way of context, the method 100 is used for aligning one or more objects (physical and/or virtual objects), which have a spatial position and orientation known in another coordinate system, with the coordinate system of the AR display. The objects can include objects (e.g., sensors and/or models representing internal anatomical structures) that are not visible within a visual field of the AR device. For example, one or more sensors have position and orientation detectable by a three-dimensional tracking system. The sensors may be hidden from sight, including positioned within a patient's body as well as be part of a marker device (e.g., embedded in the marker). The AR display may also include objects that are visible within the field of view of AR device.

One or more transforms 114 to align the tracking sensor(s) with the model coordinate system can be precomputed and stored (e.g., as a sensor-to-model space transform) in the memory 101, as shown at 114. For example, the transform 114 can be a sensor-to-model space affine transform programmed to register the tracking coordinate system in a common coordinates system with three-dimensional spatial coordinate system of a prior 3D medical image (e.g., a pre-operative CT scan). One or more anatomic models for a region of interest can be generated from the pre-operative medical image and thus be registered within the common coordinate system of the prior 3D image. As disclosed herein, the models may include a centerline model and surface model for vasculature as well as other anatomic structures of interest.

By way of further example, a pre-operative CT scan is performed to generate three-dimensional image data for a region of interest of the patient (e.g., the patient's torso). The image data may be stored in memory as DICOM images or another known format. The image data can be processed (e.g., segmentation and extraction) to provide a segmented image volume that includes the region(s) of interest for which one or more models may be generated, such the models disclosed herein. For example, the prior three-dimensional image can be acquired by preoperatively for a given patient by a three-dimensional medical imaging modality. As an example, the preoperative image data can correspond to a preoperative arterial CT scan for a region of interest of the patient, such as can be acquired weeks or months prior to a corresponding operation. Other imaging modalities can be used to provide three-dimensional image data, such as MRI, ultrasonography, positron emission tomography or the like. Such scans are common part of preoperative planning in a surgical workflow to help size prostheses and to plan surgery or other interventions.

In some examples, one or more anatomical structures captured in the preoperative image data may be converted to a respective three-dimensional model in the coordinate system of preoperative image. As an example, the model is an implicit model that mathematically describes a tubular anatomic structure (e.g., a patient's vessels), such as including a centerline and surface of the tubular structure. The implicit model may include a small set of parameters such as corresponding to a lofted b-spline (basis spline) function for the elongated anatomical structure. As one example, the anatomical model generator can be programmed to compute the implicit model data according to the disclosure of U.S. Patent Publication No. 2011/0026793 entitled Automated Centerline Extraction Method and Generation of Corresponding Analytical Expression and Use Thereof, which is incorporated herein by reference. Another example of generating an implicit model for tubular anatomical structures is disclosed in *Analytical centerline extraction and surface fitting using CT scans for aortic aneurysm repair*, Goel, Vikash R, Master's Thesis, Cornell University (2005), which is incorporated herein by reference. Other types of geometric representations can also be utilized to provide the implicit model. For example, parameters representing lofted ellipses or triangular meshes can be generated to provide the anatomical model data representing the patient's anatomical structure of interest in three-dimensional coordinate system. The three-dimensional mesh that is generated (based on three-dimensional prior image data acquired by a pre-operative medical imaging modality) may be stored in memory 101 in addition or as an alternative to the three-dimensional image acquired by the preoperative image modality. The mesh may be a static (e.g., fixed) mesh or it may vary with time, e.g., with the subject's heart beat or breathing. For example, a mesh model is generated as a four-dimensional model (in model space) to have a three-dimensional configuration that varies over time, such as gated to a biological function, such as respiration or heart rate (e.g., detected in an EKG).

An intra-operative registration phase is performed based on intraoperative image data that is acquired. The intra-operative data may be acquired prior to or during a procedure and may include 3D image data or 2D image data, such as from an intra-operative cone beam CT (CBCT) scan or another intra-operative radiographic scan (e.g., a non-CBCT registration approach disclosed in the above-incorporated U.S. application No. 62/829,394). The intra-operative registration (e.g., CBCT registration or non-CBCT registration) is performed while a marker device (e.g., a tracking pad) is attached to the patient, such as just prior or during a procedure. For example, the marker device includes one or more radio-opaque objects in the tracking pad having a known position and orientation (or pose) with respect to one or more tracking sensors, which can be used to determine tracking sensors location in the registration space. That is, the marker device enables determining a transform (e.g., a tracking system-to-intra-operative transform—also referred to herein as a first transform matrix) to spatially align the space of the tracking system with the intra-operative registration space. The intra-operative registration space is the coordinate system in which the patient resides during a procedure and that is used to acquire AR and tracking data concurrently during the procedure by the AR device and tracking system, respectively.

Another transform is determined (e.g., an intra-operative-to-pre-operative transform—also referred to herein as a second transform matrix) to spatially align the coordinate systems of the intra-operative images with the pre-operative CT scan. For example, manual registration is performed to align the bones in the CBCT scan with the bones in the pre-operative CT scan. Alternatively, an automated or semi-automated registration process may be performed. The intra-operative-to-pre-operative transform thus enables to map spatially between the intra-operative image space and the pre-operative CT coordinate space. The intra-operative-to-pre-operative transform may be combined with the tracking system-to-intra-operative transform (e.g., through matrix multiplication) to provide the tracking system-to-pre-operative transform 114 that enables spatial registration from the tracking system coordinate system to the pre-operative image coordinate system. For example, the position and orientation (or pose) for any sensor in the tracking system space (e.g., tracking sensor data 120 from the tracking system) can be mapped first from tracking system space to the intra-operative space (e.g., using the tracking system-to-intra-operative transform), then from intra-operative space to pre-operative space (using the intra-operative-to-pre-operative transform). As mentioned, the tracking system-to-intra-operative transform and intra-operative-to-pre-operative transform can be combined to provide the tracking system-to-pre-operative transform 114.

Figure 2:
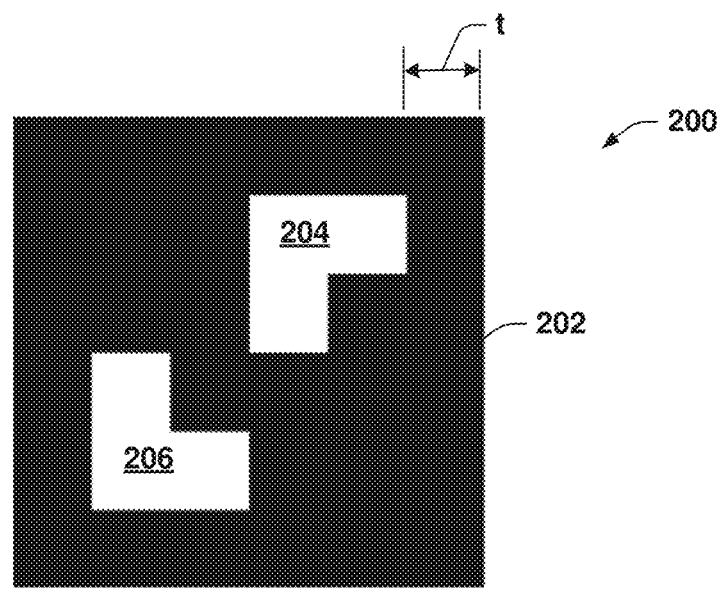
FIG. 2 depicts an example of a marker device.
Figures 3A, 3B:
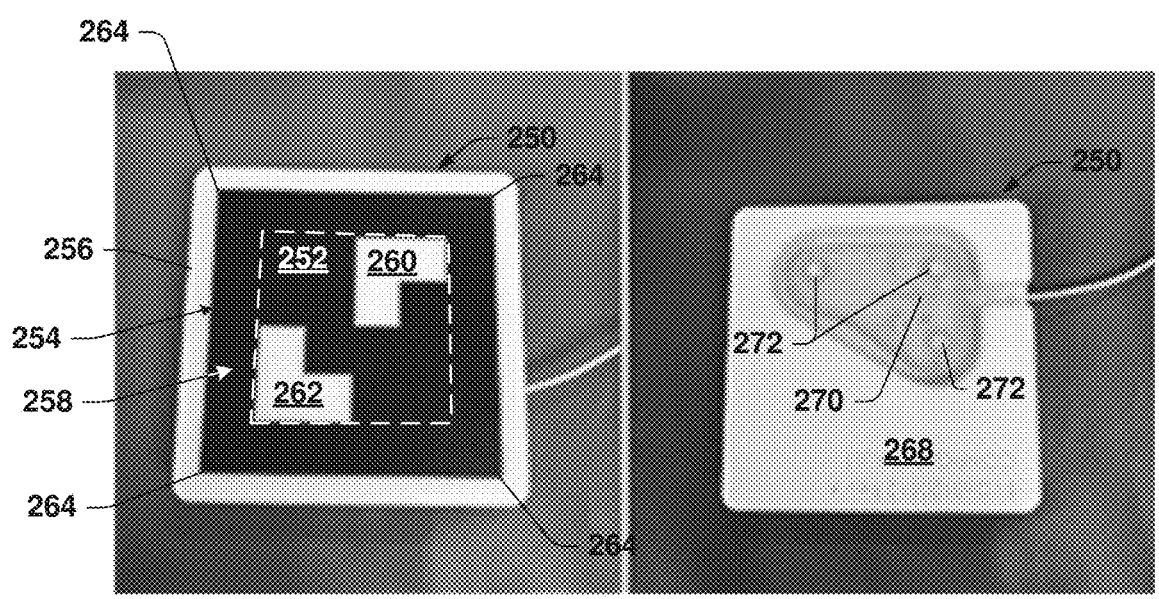
FIGS. 3A and 3B depict an example of a multi-modal marker device.

As disclosed herein, the multi-modal marker device includes one or more visible fiducial markers (see, e.g., FIG. 2) and one or more tracking sensors integrated into a common fixed structure (see, e.g., FIGS. 3A and 3B). The fixed structure of the marker device provides the fiducial marker(s) and tracking sensor(s) a known spatial relationship and orientation (e.g., a fixed spatial offset) with respect to each other in three-dimensional space, which relationship can be stored in memory as tracking sensor data, demonstrated at 112. The fiducial markers on the multi-modal marker includes one or more marker patterns (see, e.g., FIG. 2) that are visible in images acquired by respective cameras (see, e.g., FIG. 4) that have a fixed position with respect to the AR device. The images may be in the visible light spectrum or another spectrum outside of the visible light spectrum (e.g., infrared) that can be captured in the images acquired by the cameras at 102. The position and orientation for each camera with respect to the coordinate of the AR device can be stored in the memory 101 as camera position data, demonstrated at 108. As an example, the cameras can be implemented as a set of forward-facing cameras mounted at respective fixed positions of a frame of a display of the AR device (e.g., at spaced apart locations along a front of head mounted display).

As a further example, the marker device includes one or more sensors configured to indicate a three-dimensional position in a coordinate system of the tracking system. For example, the tracking system is an electromagnetic tracking system that generates an electromagnetic field. Each sensor provides a sensor signal based on the electromagnetic field, which is converted into position and orientation information for each respective sensor. An example electromagnetic field tracking system is commercially available from Northern Digital, Inc., of Ontario, Canada. The tracking system can provide the tracking data at an output sample rate (e.g., sixty samples per second) for each sensor sufficient to enable substantially real time determination of sensor location (e.g., to provide a vector describing sensor position and orientation). The tracking system thus can process each frame of tracking data such that the tracking data can likewise represent real time tracking data acquired by the tracking system, which can be registered into a coordinate system of an imaging system, as disclosed herein. In some examples, each sensor can be detectable by the tracking system to enable tracking the sensor in five or six degrees of freedom. Other types of sensors and tracking systems may be used in other examples.

In this example context, at 102, the method includes acquiring images from each of the cameras mounted to the AR device (e.g., AR headset 308). Each of the cameras may be configured to acquire respective images for a field of view that is overlapping with each other. For instance, where the AR device includes two cameras, first and second images are acquired. The images may be acquired and be continually updated over time at an imaging sample rate, which may correspond to the native sample rate of the cameras or a multiple thereof. For purposes of this example it is presumed that the images acquired at 102 include at least one fiducial marker of the multi-modal marker while such marker is placed adjacent or attached to a patient's body.

Figure 4:
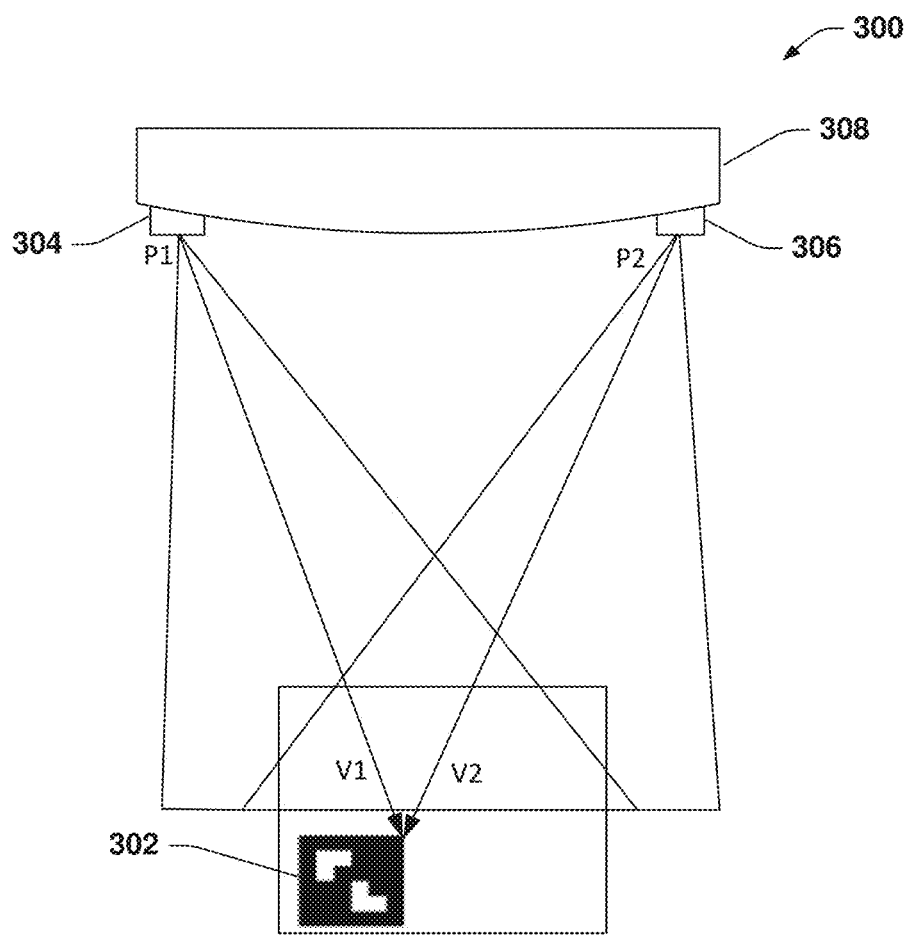
FIG. 4 depicts example of an augmented reality device including cameras to acquire two-dimensional images of a visualization space.

At 104, image processing is performed (e.g., by marker identification function 444) to identify the fiducial marker(s) in each of the images acquired at 102. There can be any number of total images for each sample time—one from each camera. As one example, the visible fiducial marker is provided on a surface of the marker device in a form of an ArUco marker (see, e.g., Open Source Computer Vision Library: http://opencv.org). An example of such a fiducial marker is shown in FIGS. 2, 3A, and 4. In this way, an image processing algorithm (e.g., detectMarkers( ) function of the OpenCV library) may implemented to detect and identify each such fiducial marker at 104. In an example with a different type of marker other image processing techniques may be used to localize the marker. The marker identification at 104 may be fully automated and/or be user-interactive in response to a user input identifying the markers. The identified markers (e.g., pixel locations in the respective images) may be stored in the memory 101 for further processing.

At 106, a three-dimensional position is estimated (e.g., by marker point generator 446) for respective predetermined portions of the fiducial marker with respect to a coordinate system of the AR device. The three-dimensional position is determined based on the locations of such predetermined portions in each of the respective images (determined at 104) and based on the AR camera position data 108. The fiducial marker(s), which is represented in the images acquired from the cameras at 102, may be include a pattern that includes a rectangular-shaped (or other identifiable shaped) marker border having respective corners where edges thereof meet. For the example of the combination marker that includes an ArUco type marker visible to the camera, the spatial coordinates may be generated for each of the corners of each marker, namely, coordinates for a set of four points surrounding each tracking sensor. Additionally, locations of respective corners from each image that includes a representation of the ArUco-type fiducial marker can be determined, such as disclosed herein (see, e.g., description relating to FIG. 4). FIG. 4 and the corresponding description demonstrate an example of how respective corners of such fiducial marker may be located in three-dimensional coordinates of the AR space.

At 110, an affine transform is computed (e.g., by zero transform calculator 462) to align a coordinate system of the tracking system with the AR coordinate system. The transform computed at 110 may be stored in the memory 101 (e.g., corresponding to zero transform matrix 410). The affine transform generated at 110 thus may be applied directly to register tracking data from the tracking system space to the AR coordinate space and/or to register AR data from the AR coordinate space to the tracking system space. The affine transform determined at 110 can be derived based on the estimated position for the predetermined portions of the marker(s) determined at 106 and the tracking sensor data 112. As mentioned, the tracking sensor data 112 may represent a known, fixed three-dimensional spatial relationship of the predetermined portions of the marker(s) and the tracking sensor(s) of the marker device. As an example, the fixed relationship of the predetermined portions of the marker(s) and sensors may be determined during manufacturing and printed on the marker. As another example, the relationship may be measured and entered into a computer (e.g., via user interface) that is programmed to determine the transform at 110.

At 116, the affine transform determined at 110 as well as one or more other transforms 114 are applied to one or more models (e.g., 3D mesh structures) and to tracking position data (for one or more sensors) to place such models and sensors in the coordinate system of the AR display. For the example when the models are generated from the high resolution pre-operative CT scans, each of the models to be used by the AR device (e.g., centerline model, a surface mesh model) are naturally expressed in the pre-operative coordinate space. To place such models in the proper location so that they overlap the real-world object in the AR display, the affine transform determined at 110 is combined with one or more other transforms 114 to map into the AR coordinate system where the AR device is currently being used. The other transforms 114 may include a first transform (e.g., first transform matrix 412) programmed to register between an intra-operative image coordinate system and the tracking system coordinate space. Additionally or alternatively, the other transforms 114 may include a second transform (e.g., second transform matrix 414) programmed to register between the intra-operative image coordinate system and the coordinate system of a prior 3D image (e.g., pre-operative image space). The particular way in which the method 100 applies each of the transforms 110 and 114 (or inverse thereof) at 116 depends on the ultimate visualization space and the domain of the data being co-registered in such visualization space. The domain may be recognized automatically, such as based on the type of data or metadata describing the domain, and/or it may be specified by a user in response to a user input. In the following example, it is presumed that the visualization space is the AR coordinate system.

At 118, the AR visual field is displayed on the AR display, which may include computer-generated models at positions that overlap (e.g., are superimposed graphically) real-world objects at 3D spatial positions determined from applying the method 100 to the models and other input data. From 118, the method returns to 102 and is repeated to update the affine transform at 110 based on changes in the images that are acquired 102. In this way, the AR visual field (e.g., the hologram) is continually updated in real time so that the hologram that is generated on the AR display spatially and temporally aligns with internal anatomical structures of the patient's body, even when such structures are not actually visible. As disclosed herein, for example, the method 100 operates to align internal anatomical structures (that are not visible in the real world) with the patient's body in the spatial coordinate system of the AR display, which may be moving with respect to the patient's body. Advantageously, by implementing the method 100, the transform computed at 110 changes in response to changing information in the acquired images at 102; however, the other transforms (including transform 114) may remain unchanged such that the associated computations may be executed more efficiently in real-time.

By way of example when rendering the output visualization at 118 in the AR spatial domain, models for the bones and vasculature (e.g., generated from in prior 3D image space) may be rendered in the AR display by applying multiple transforms (e.g., inv(T0)*inv(T1)*inv(T2)) and anything tracked in EM space (catheters, guidewires, etc.) would have a single transform applied (e.g., inv(T0)). In an example, when rendering the visualization in the prior 3D image space, the models for the bones and vasculature (being in the pre-op CT image space) would require no transforms to be applied whereas anything being tracked in tracking system space (e.g., objects having one or more tracking sensors, such as catheters, guidewires, etc.) would have two transforms applied (e.g., T1*T2). For example, as disclosed herein, the transforms may be applied through matrix multiplication to map data from one spatial domain to another spatial domain.

As a further example, the AR device (e.g., AR device 308) may be implemented as an AR headset (e.g., Hololens or Hololens2 from Microsoft or other smart glasses). In such AR headsets, the AR device is constantly refining its map of the surrounding environment. Consequently, holograms that are generated in the AR visual field have a tendency to "drift" from their original locations. The "drift" can be problematic when precise alignment is needed, such as for medical applications. Accordingly, the method 100 continually updates the transform at 110 based on the acquired images at 102 provided as image streams from the front-facing cameras of the AR headset. Additionally, by using two non-parallel cameras, the position of the corners of the markers can be estimated accurately by computationally efficient triangulation (reducing the CPU load) and updated constantly. This enables "drift" to be corrected without requiring re-registration.

FIG. 2 depicts an example of a fiducial marker 200. As shown in this example, the marker includes black and white colors (e.g., binary) and includes a thick black rectangular (e.g., square) border 202 along each side of its entire peripheral edge (e.g., having a thickness "t", such as one or more pixels thick). An interior of the marker 200 includes white symbols 204 and 206 that can be used to define an orientation and/or other identifying feature that may be associated with the marker, such as according to an ArUco library.

FIGS. 3A and 3B depict an example of a multi-modal marker device 250. The multi-modal marker device 250 can be placed near a patient (e.g., next to or on the patient)) during the acquisition of the first and second images (e.g., at 102). For example, the multi-modal marker device 250 can be placed in a visibly unobstructed surface (e.g., on a hospital bed) or attached to the patient's body during a procedure. FIG. 3A shows one side surface 252 of the marker 250 that includes a fiducial marker (e.g., the marker of FIG. 2) 254 located within a white colored border 256 to provide contrast between the white border and a thick black border 258 of the fiducial marker (e.g., extending between dotted line and the white border 256). Symbols 260 and 262 are on the fiducial marker spaced apart from the black border 258.

The example of FIG. 3B is view from of same marker 250 showing the other side surface 268. In FIG. 3B, one or more tracking sensors (e.g., electromagnetic sensors) 270 are attached to the marker device 250 at known positions and orientations relative to the corners 264 of the fiducial marker 254. In one example, the one or more sensors 270 can respectively spatially sense a plurality of degrees of freedom (DOF). For example, the one or more sensors 270 can be configured to sense six (6) DOF. In one example, the sensors 270 can be localized using an electromagnetic tracking system, such as disclosed herein. The tracking system allows for determination of position and orientation of each sensor 270 based on a sensor signal, such as provided from the sensor to the tracking system in response to an electromagnetic field.

FIG. 4 depicts a schematic example of a camera system 300 that can be used to acquire two-dimensional images of a fiducial marker 302 from multiple non-parallel viewing angles. For example, camera system 300 includes a pair of forward-facing cameras 304 and 306 integrated to a front panel of an AR headset 308. For example, the cameras 304 and 306 may be implemented as digital grayscale cameras to acquire images of objects in a visible portion of the spectrum. In other examples, cameras 304 and 306 may acquire images outside of the visible spectrum and the fiducial marker 302 may be invisible to the user's eye. Because the cameras 304 and 306 are attached to a headset or other portable device 308, the images acquired by each camera may vary over time based on movement of the user. For example, as the user's head moves while wearing the AR headset 308, the viewing angle will likewise move commensurately, thereby changing the position of the fiducial marker in each image.

By way of example, the registration is performed by modeling each of the cameras 304 and 306 as an ideal pinhole camera (e.g., assuming no distortion), where each pixel in the resulting image is formed by projecting 3D points into the image plane using a perspective transform such as follows:

$$s \begin{bmatrix} u \\ v \\ 1 \end{bmatrix} = \begin{bmatrix} f_x & 0 & c_x \\ 0 & f_y & c_y \\ 0 & 0 & 1 \end{bmatrix} \begin{bmatrix} r_{11} & r_{12} & r_{13} & t_1 \\ r_{21} & r_{22} & r_{23} & t_2 \\ r_{31} & r_{32} & r_{33} & t_3 \end{bmatrix} \begin{bmatrix} X \\ Y \\ Z \\ 1 \end{bmatrix}$$

where:
X, Y, and Z are the coordinates of a 3D point in the common coordinate system;
u and v are the coordinates of the projection point in the camera image in pixels;
fx and fy are the focal lengths in pixel units;
cx and cy is the image center in pixel units; and
r ## and t # define the position and orientation, respectively, of the camera in the common coordinate system.

To create the vector v1 or v2, the corners of the fiducial marker 302 (e.g., an ArUco type marker) are located in the image as u and v. The remaining values of the equation can be filled in based on the known spatial locations, and the equation is solved for X and Y at the focal length (e.g., distance between the camera and the respective corner location). The vector is then computed by subtracting the camera's position (p1 or p2) from this new location. For example, points p1 and p2 are defined based on position of the headset 308. The focal length of the camera is measured during device calibration.

The 3D position of the corner of the marker 302 can then be computed by finding the intersection (or nearest approach) of the two vectors v1 and v2. The position and orientation of the ArUco marker in the common coordinate system is computed by repeating this process for all four corner locations identified for the fiducial marker in each of the respective images. By way of example, intersection (or nearest approach) of the two vectors may be computed according to the following pseudo-code:

```
vector ClosestPoint(vector p1, vector v1, vector p2, vector v2)
{
  // normalize direction vectors
  v1 = normalize(v1);
  v2 = normalize(v2);
  // check that the vectors are not co-incident (parallel)
  float projDir = dot_product(v1, v2);
  if (absolute_value(projDir) > 0.9999f)
  {
    // vectors are nearly co-incident (parallel)
    return p1;
  }
  // compute nearest point
  float proj1 = dot_product(p2 - p1, v1);
  float proj2 = dot_product(p2 - p1, v2);
  float dist1 = (proj1 - (projDir * proj2)) / (1 - (projDir * projDir));
  float dist2 = (proj2 - (projDir * proj1)) / ((projDir * projDir) - 1);
  vector pointOnLine1 = p1 + (dist1 * v1);
  vector pointOnLine2 = p2 + (dist2 * v2);
  return linear_interpolate(pointOnLine1, pointOnLine2, 0.5f);
}
```

The estimated position of the corners of the marker (e.g., determined at 106) and the respective transform (e.g., determined at 110) thus can be used to enable rendering one or more visualizations in the AR field of view.

As one example, the transform generated as disclosed herein may be implemented by a registration engine (e.g., registration manager 494) to register tracking data from one or more tracking sensors into the AR visual coordinate system to provide registered tracking data. An output generator (e.g., output generator 512) executing on the AR device or a computer to which the AR device is linked can utilize the registered tracking data and model data to provide corresponding output visualization that is graphically rendered on a display (e.g., display 510), in which the models are visualized as holographic overlays in the AR visual space positioned over the patient's body.

Figure 5:
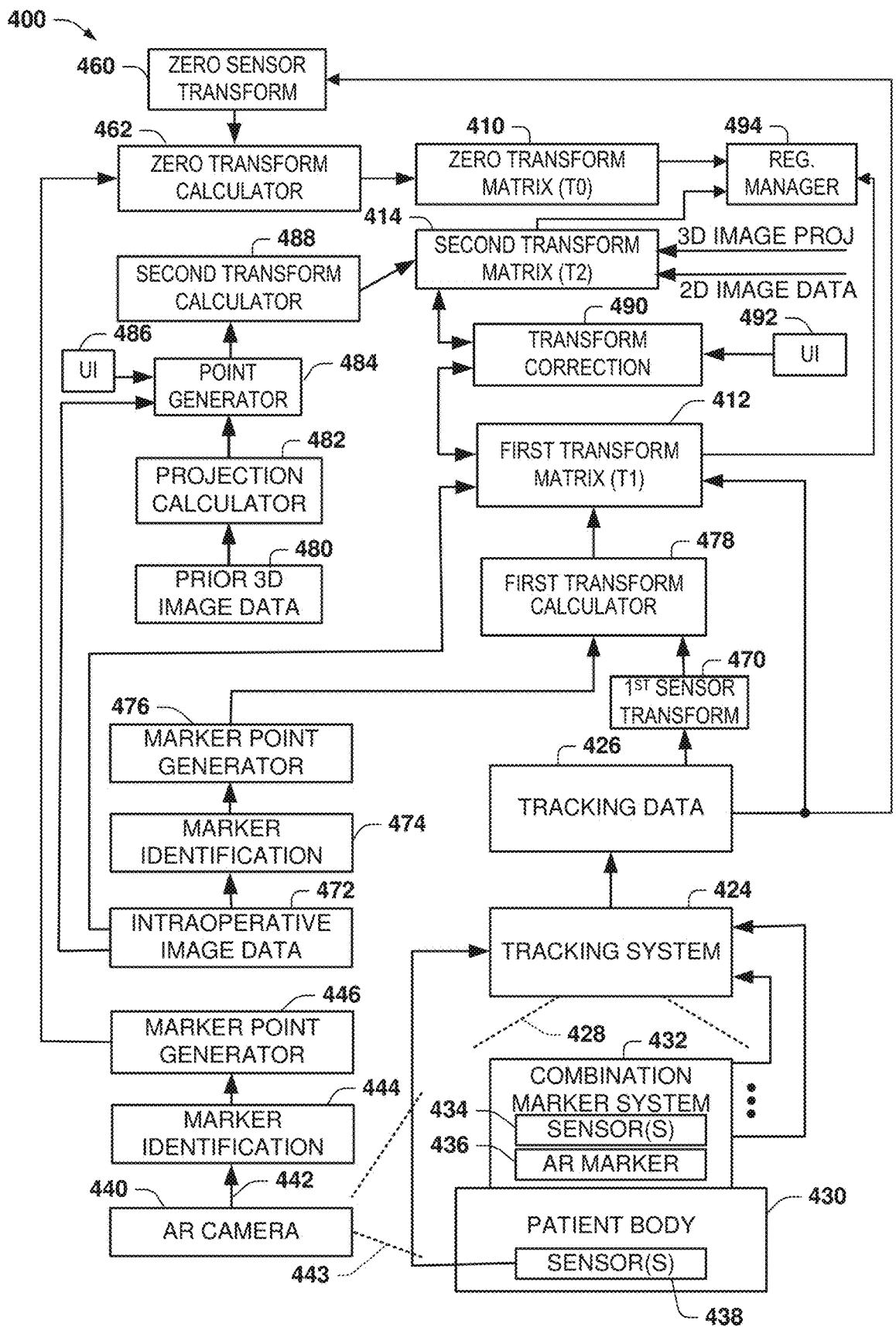
FIG. 5 depicts an example of a system for generating affine transformations.

FIG. 5 depicts an example of a system 400 for generating affine transformations. In this example, the affine transformations are demonstrated as transform matrices 410, 412 and 414 for registering tracking data, models and image data, as disclosed herein. The system 400 is described in the context of data and instructions, and a processor can access the data and execute the instructions to perform the functions disclosed herein. It is to be understood that not all functions may be required to implement the system. For example, each of the different transform matrices may be separately generated, which affords advantages when an imaging modality changes or is replaced in another implementation, as the entire system does not need to be modified.

In the example of FIG. 5, the system 400 is configured to execute program code to generate a zero transform matrix (T0) 410. The transform matrix T0 may be configured to transform from a tracking system coordinate system of a tracking system 424 into an AR coordinate system of an AR device and/or from the AR coordinate system to the tracking coordinate system. As disclosed herein, the AR device includes two or more AR cameras 440. As examples, the AR device may be implemented as AR headset, smart phone, tablet computer or other mobile device. The cameras 440 may be integrated into or otherwise coupled and at a known position with respect to the AR device. Each camera 440 provides AR image data for a respective field of view 443, such as may at least one AR marker 436 of a multi-modal marker device (e.g., marker device 250). The tracking system 424 is configured to provide tracking data 426 to represent a position and orientation of one or more marker tracking sensors 434 and/or object tracking sensors 438.

For example, a combination marker system 432 (e.g., including one or more multi-modal marker devices of FIG. 3A, 3B, or 4) can be attached to the patient's body 430 or placed near the patient' body. In the example of FIG. 5, the combination marker system 432 can include one or more marker tracking sensors 434 that provide marker tracking data representing a location and orientation of each marker device within the coordinate system of the tracking system 424. In an example, the one or more object sensors 438 can be affixed relative to an object that is movable within the patient's body 430 for identifying a location of such sensor in the coordinate system of the tracking system. For example, each marker tracking sensor 434 provides a signal (e.g., induced current) responsive to an electromagnetic field generated by a field generator of the tracking system 424. Each such object sensor 438 may be affixed to an object (e.g., guidewire, catheter or the like) that is moveable within the patient's body 430. The object tracking sensor 438 thus can also provide a signal to the tracking system 424 based on which the tracking system 424 can compute corresponding tracking data representative of the position and orientation of such sensor (and the object to which it is attached) in the tracking system coordinate system. As mentioned, the tracking data 426 thus represents a position and orientation of each respective object tracking sensor 438 as well as marker tracking sensors 434 of the multi-modal marker system 432.

By way of example, the tracking system 424 can include a transmitter (e.g., an electromagnetic field generator) that provides a non-ionizing field, demonstrated at 428, which is detected by each sensor 434 and 438 to provide a corresponding sensor signal to the tracking system. An example tracking system 424 is the AURORA spatial measurement system commercially available from Northern Digital, Inc., of Ontario, Canada. The tracking system 424 can provide the tracking data 426 at an output sample rate (e.g., sixty samples per second) for each sensor sufficient to enable substantially real time determination of sensor location (e.g., to provide a vector describing sensor position and orientation). A tracking processing subsystem of system 424 thus can process each frame of tracking data such that the tracking data can likewise represent real time tracking data acquired by the tracking system that can be registered into another coordinate system by applying one or more of the generated transforms 410, 412 and/or 414 to enable generating a graphical representation in a given spatial domain, as disclosed herein. The tracking system 424 may provide the tracking data 426 with an output sample rate to enable computation of real time positioning and visualization of the object to which the sensor is attached as well as the combination marker system.

A zero sensor transform 460 is configured to convert the tracking data 426 into locations the AR marker 436 that is implemented on each respective marker device, such as disclosed herein. The transform 460 provides each of locations as 3D spatial coordinates in the tracking system coordinate space and may remain fixed if the marker device does not move in the tracking space or may vary over time if the marker device moves in tracking space. For example, in the tracking coordinate system, each AR marker of a given marker device are at fixed, known offsets (e.g., a 3D vector) from the location of the marker tracking sensor 434 that is part of the given marker device of marker system 432. As mentioned, the marker system may include a plurality of multi-modal marker devices, such as ArUco type (e.g., device 250), or other marker configurations as disclosed herein.

As an example, the sensor transform 460 thus is configured to compute the points (e.g., 3D coordinates for marker locations) in the tracking system space based on the tracking data 426 and the known offsets for each tracking sensor relative to the predetermined marker locations. For the example of the ArUco type multi-modal marker device, the marker locations may be a set of four points (e.g., emPoint_1, emPoint_2, emPoint_3, emPoint_4) at the corners of the marker, such as disclosed herein. For example, the points in tracking system space for a set of marker locations of the ArUco type marker device having a sensor providing tracking data 426 may be computed for a given marker device by multiplying the sensor transform (TS), which includes tracking sensor 3D coordinates and the respective offset, as follows:

emPoint_1=mult(TS, offset_1),
emPoint_2=mult(TS, offset_2),
emPoint_3=mult(TS, offset_3), and
emPoint_4=mult(TS, offset_4)

The points determined by the sensor transform 460 for the AR marker 436 may be arranged in a set of point for each respective marker device (if more than one marker device) or as a single set that contains all the points.

As mentioned, each AR camera 440 provides the AR camera data 442 for an AR field of view 443. For example, the AR field of view 443 may include one or more AR marker 436, such as is on an exposed surface of a multi-modal marker device that also includes one or more marker tracking sensor 434. The sensor transform 460 thus provides the 3D spatial coordinates in the tracking coordinate system for the points on the same AR marker that is visible in image represented by the AR camera data 442.

As a further example, the system 400 includes a marker identification function 444 (e.g., executable instructions, such as corresponding to the identification at 104) that is configured to locate each marker (e.g., ArUco marker or other type of marker) in each image frame provided in the AR image data 442. For the example of the combination marker that includes an ArUco type marker, the function 444 may invoke an ArUco detection function to locate each respective marker. For an example combination marker that includes a marker other than an ArUco type marker, a periphery or other features of such marker may thus be localized by image thresholding as well as other image processing techniques (e.g., feature extraction) applied to image pixels in the AR images 442. The marker identification function 444 may be fully automated. The identified markers (e.g., pixel locations in the respective images) may be stored in memory for further processing.

A marker point generator 446 is programmed to generate spatial coordinates for portions of each marker identified in the (e.g., two or more) images provided by the image data 442. For the example of the marker device that includes an ArUco type marker, the spatial coordinates may be generated for corners of each marker, namely, coordinates for a set of four points (e.g., surrounding or otherwise having a known relative position to a tracking sensor). As an example, the marker point generator for example, is programmed to execute a closest point function (e.g., the ClosestPoint( ) function, such as disclosed herein), to locate the set of points around each respective tracking sensor for the marker device. Each set of points for a given AR marker 436 can be linked and associated with a respective marker tracking sensor 434 to facilitate generating the transform matrix 410.

A zero transform calculator 462 is programmed to compute the zero transform matrix 410 based on the points (spatial coordinates) provided by the marker point generator 446 in the AR spatial domain and the points (spatial coordinates) provided by a zero sensor transform function 460 in the tracking spatial domain. The points thus represent the same portions of the AR marker in different coordinate systems. For example, the transform calculator 462 is programmed to align (e.g., co-register) the sets of points that have been measured in each of the spatial coordinate systems. Examples of such co-registration algorithm implemented by the transform calculator 462 to co-register the points in the respective domains (e.g., tracking system coordinate system and AR coordinate system) may include an error minimization function or a change of basis function.

As one example, the transform calculator 462 is programmed to implement an error minimization function. Given the ordered set of points, the transform calculator 478 is to determine unknown transform T0 that minimizes the distance between the projected AR location and the measured location. For example, for T1 the transform calculator 462 is programmed to find the transform that minimizes the distance between points, such as follows:

sum(n=1 . . . i, distance(mult(T1, arPoint_n), emPoint_n)^2)

where: n denotes a given one of i points (i is the number of points for a given multi-modal marker;
arPoint_n is the spatial coordinates in AR image space for point n; and
emPoint_n is the spatial coordinates in tracking space for point n.

In an example, the error minimization can be solved through Single Value Decomposition or any number of error minimization algorithms.

As another example, the transform calculator 462 is programmed to implement a change of basis function to derive the zero transform matrix 410. In an example of the AR marker being an ArUco marker, the corners of the AR marker are arranged in a way that enables a set of basis vectors to be generated (x, y, and z unit vectors that define the coordinate space). For example, rather than minimizing the errors, the transform calculator 462 is programmed to find the basis vectors in both coordinate systems and apply them at a common point. This is computationally more efficient than the error minimization approached mentioned above, but requires a specific arrangement of points.

By way of example, to unambiguously define the basis vectors, the arrangement needed is 3 points forming a 90 degree angle, with enough additional information to allow us to identify which point is which (for example, having the legs of the triangle created by the 3 points be different lengths). The ArUco-type marker shown in FIGS. 2, 3A and 4 have arrangements of points sufficient enable the use of such change of basis function.

In each coordinate system, the transform calculator 462 constructs the basis vectors from 3 points. For example, given point_1, point_2, and point_3 (e.g., vertices of a right triangle), provides two segments, one from point_2 to point_1 and another from point_2 to point_3, which segments are the legs of a right triangle. These points and segments provide the following basis vectors:

basis_z=normalize(point_1−point_2)
basis_x=normalize(point_3−point_2)
basis_y=cross(basis_x, basis_z)

From the basis vectors, the transform calculator 162 is programmed to create a matrix (e.g., a 4×4 matrix) that defines the position and orientation of point_2 as follows:

matrix (point_2) = [basis_x.x, basis_y.x, basis_z.x, point_2.x, basis_x.y, basis_y.y, basis_z.y, point_2.y, basis_x.z, basis_y.z, basis_z.z, point_2.z, 0, 0, 0, 1]

With that matrix defined in each coordinate system, the transform calculator 462 can compute the transform matrix 410 between the two coordinate systems. For example, for the transform matrix T0:
 ar_Matrix is the matrix defined from the basis vectors in the AR coordinate system; and
 em_Matrix is the matrix defined from the basis vectors in the tracking coordinate system.
From the above, the transform calculator 462 may determine the transform matrix (T0) 410 by multiplying the basis vector tracking matrix (em_Matrix) and the inverse of the basis vector AR matrix (inv(ar_Matrix)), such as follows:
 T0=mult(em_Matrix, inv(im_Matrix))
The transform matrix 410 may be stored in memory and used for transforming from the tracking system space to the AR display space. For example, the position of the object sensor 438 within the patient's body, as represented by tracking data 426, may be registered into the AR space by applying the transform T0 to the position and orientation information of the tracking data. As mentioned, the transform T0 may be updated continually in real time such as to compensate for movements of the AR camera's field of view relative to the AR marker and/or if the multi-modal marker is moved (e.g., relative to the patient's body or the AR camera. In some examples, the system 400 may be configured to generate additional transform matrices 412 and/or 414 to enable co-registration of additional data and visualization in the coordinate system of the AR display as well as in other coordinate systems. In other examples, the other transform matrices 412 and/or 414 may be precomputed or not generated.

In the example of FIG. 5, the system is also configured for generating a first transform matrix (T1) 412. The transform matrix T1 may be configured to transform from the tracking system coordinate system of tracking system 424 into a coordinate system of a medical imaging modality 456 (e.g., a 2D imaging system such as fluoroscopy or x-ray) and/or from the coordinate system of the medical imaging modality to the tracking coordinate system. In an example, the marker system 432 includes one or more marker devices, including a marker tracking sensor 434, which may be attached to the patient's body 430, such that the tracking system 424 computes the tracking data 426 for such tracking sensor to accommodate for movement in the patient's body 430 in the coordinate system of the tracking system 424.

In some examples, such as for purposes of generating the transform matrix 410 and/or transform matrix 412, the object tracking sensor(s) 438 and corresponding tracking data 426 may be ignored (or omitted). In other examples, the object tracking sensor 438 may be placed at a known location with respect to the patient's body 430 (e.g., a known anatomical landmark within or external to the patient's body) to provide additional data points, in both the tracking system spatial domain (e.g., provided by tracking data 426) and a spatial domain of one or more imaging modalities (e.g., in intraoperative image data 472) so long as the location where it is placed is visible in an image generated provided by the modality that generates such data. In an example, an intraoperative medical imaging modality (e.g., fluoroscopy or other x-ray) provides the image data 472 (e.g., including a known location of the object tracking sensor 438) that may be used to facilitate generating the transform matrix (T1) 412.

A first sensor transform 470 is configured to convert the tracking data 426 into locations for radiopaque objects implemented on each respective marker device, such as disclosed herein. Each of locations are 3D spatial coordinates in tracking system coordinate space and may remain fixed if the marker device does not move in the tracking space or may vary over time if the marker device moves in tracking space. For example, in the tracking coordinate system, each of the radiopaque markers of a given marker device are at fixed, known offsets (e.g., a 3D vector) from the location of the tracking sensor 434 that is part of the given marker device of marker system 432. As mentioned, the marker system may include a plurality of multi-modal marker devices, such as ArUco type (e.g., device 250), or other marker configurations (e.g., AR device 308) as disclosed herein. The multi-modal marker device may thus include radiopaque elements visible in the image data 472, AR elements visible in the AR image data 442 and tracking sensor(s) detectable by the tracking system. The radiopaque elements may be in the form of radiopaque ArUco type markers and/or as radiopaque spheres 272, such as shown in FIG. 3B.

The sensor transform 470 thus is configured to compute the points (e.g., 3D coordinates for marker locations) in the tracking system space based on the tracking data 426 and the known offsets for each tracking sensor relative to the predetermined marker locations. For the ArUco type multi-modal marker device, the marker locations may be a set of four points (e.g., emPoint_1, emPoint_2, emPoint_3, emPoint_4) at the corners of the marker, such as disclosed herein with respect to sensor transform 460.

For the example of a marker device (e.g., for marker device 250 of FIG. 3B) that includes an arrangement of spherical radiopaque markers, there are 3 spherical markers at known offsets distributed around each tracking sensor 270. Accordingly, the sensor transform 470 will generate three points for each marker device in the marker system 432. For example, the transform 470 can determine marker locations at points (e.g., emPoint_1, emPoint_2, emPoint_3) located at the center of each of the spherical marker based on multiplying the respective transform and the known offset (e.g., 3D offset vector) between the tracking sensor location (e.g., a 3D point) and the respective radiopaque objects, such as follows:
 emPoint_1=mult(Ts, offset_1),
 emPoint_2=mult(Ts, offset_2), and
 emPoint_3=mult(Ts, offset_3).
Other deterministic locations having fixed offsets associated with the radiopaque markers may be used in other examples. In some examples the points may be arranged in a set of point for each marker device or as a single set that contains all the points.

The image data 472 may be generated as 2D or 3D data representing objects within a field of view 475 of the imaging modality. For example, the imaging modality may include a cone beam CT, a fluoroscopy scanner or other medical imaging modality. In one example, the image data 472 is 2D image data for a small number of (e.g., at least two, three or four) 2D projection images acquired at different viewing angles relative to the patient's body 430. In some examples, the region of the patient's body may be a region of interest in which the object sensor 438 is to be moved, such as part of a surgical procedure.

A marker identification function 474 can be configured to locate each radiopaque marker (e.g., ArUco marker and/or other object marker) in the image data 472. The radiopaque markers will be visible in the images due to their opacity with respect to the ionizing radiation emitted by the imaging modality 456. For the example of the combination marker that includes an ArUco type marker, the marker identification function 474 can invoke an ArUco detection function to locate each respective marker. For an example combination marker that includes a radiopaque object other than an ArUco type marker, a periphery of each such marker may thus be localized by image thresholding as well as other image processing techniques applied to values of image pixels. The marker identification function 474 may be fully automated and/or be user-interactive in response to a user input identifying the markers. The identified markers (e.g., pixel locations in the respective images) may be stored in memory for further processing.

A marker point generator 476 is programmed to generate spatial coordinates for each marker that the marker identification function 474 has identified in the image data 472. For the example of the combination marker that includes a radiopaque ArUco type marker, the spatial coordinates may be generated for each of the corners of each marker, namely, coordinates for a set of four points surrounding each tracking sensor. For spherically shaped radiopaque markers, the spatial coordinates for each marker are provided as 2D coordinates at a center of the circular projection (e.g., the periphery identified by marker identification function 474) in each 2D image for the viewing angle provided by the field of view 475 relative to the marker system 432. In an example where three spherical markers surround each tracking sensor for a given marker device, the marker point generator 476 is programmed to provide coordinates for a set of three points for the given marker device. Regardless of the type and configuration of radiopaque marker, the marker point generator 476, for example, is programmed to execute a closest point function such as disclosed herein, to locate the set of points around each respective tracking sensor for the marker device. In this way, each set of points can be linked together and associated with a respective one of the tracking sensors to facilitate generating the first transform matrix 412.

A first transform calculator 478 is programmed to compute the first transform matrix 412 based on the points provided by the marker point generator 476 and points provided by the sensor transform function 470. For example, the transform calculator 478 is applied to align the sets of points that have been measured in the spatial coordinate systems. Examples of such co-registration algorithm to co-register the points in the respective domains (e.g., tracking system coordinate system and medical imaging coordinate system) may include an error minimization function or a change of basis function, such as disclosed herein.

As one example, the transform calculator 478 is programmed to implement an error minimization function. Given the ordered set of points, the transform calculator 478 is to determine unknown transform T1 that minimizes the distance between the projected location and the measured location. For example, for T1 we want to find the transform that minimizes the distance between points, such as follows:

sum(n=1 . . . i, distance(mult(T1, imPoint_n), emPoint_n)^2)

where: n denotes a given one of i points (i is the number of points for a given multi-modal marker;

imPoint_n is the spatial coordinates in image space for point n; and emPoint_n is the spatial coordinates in tracking space for point n.

In an example, the error minimization can be solved through Single Value Decomposition or any number of error minimization algorithms.

As another example, the transform calculator 478 is programmed to implement a change of basis function, such as disclosed herein with respect to the transform calculator 462. As mentioned, where applicable, the transform calculator 478 is programmed to implement a change in basis function, which is computationally more efficient than the error minimization approached mentioned above. Both the ArUco-type marker of FIGS. 3A and 3B have arrangements of points sufficient enable the use of such change of basis function, with the caveat being that for the radiopaque marker device of FIG. 3B, each set of 3 points for each marker device is to be treated separately. With that matrix defined in each coordinate system, the transform calculator 478 can compute the transform 412 between the two coordinate systems. For example, for the transform matrix T1:

im_Matrix is the matrix defined from the basis vectors in the medical imaging (e.g., intraoperative) coordinate system; and em_Matrix is the matrix defined from the basis vectors in the tracking coordinate system.

From the above, the transform calculator 478 may determine the transform matrix (T1) 412 by multiplying the basis vector tracking matrix (em_Matrix) and the inverse of the basis vector imaging matrix (inv(im_Matrix)), such as follows:

T1=mult(em_Matrix, inv(im_Matrix))

The transform matrix may be stored in memory and used for transforming from the tracking system space to the medical imaging space. For example, the position of the object sensor 438 within the patient's body, as represented by tracking data 426, may be registered into the medical imaging space by applying the transform T1 to the position and orientation information of the tracking data.

As mentioned, the system 400 also is configured to generate the second transform (T2) 414 for use in transforming between the medical imaging coordinate system for intraoperative image data 472 and a coordinate system of prior 3D image data 480. For example, the prior 3D image data 480 may be stored in memory (e.g., as a DICOM image set) and include a 3D image from a preoperative scan (e.g., CT scan) of the patient's body 430 that is performed at a time prior to when the medical imaging modality 456 generates its image data 472 (e.g., intraoperatively, such as corresponding to images acquired at 102 and 104).

In some examples, such as where the intraoperative image data is provided as a small number of 2D image projections, the system includes a projection calculator 482. The projection calculator 482 is programmed to generate a respective projection from the 3D image data 480 for each of the images (e.g., two images) provided in the 2D image data 472. The projection calculator 482 implements a function to map the points from the 3D image space onto a two-dimensional plane. For example, the projection calculator derives forward projections that are aligned with the viewing angles of the images in the 2D image data 472. The registration of projection angles for each of the 3D projections may be implemented through manual alignment and/or be automated. In an example, the alignment may be automated, such as based on image metadata (demonstrated as included in the arrow from the 2D image data 472 to projection calculator 482) in the image data 472 that describes the angle of each of the 2D images. For example, the metadata includes data specifying the projection angle, such as AP, LAO, RAO, such as may be known from the angle of a C-arm and/or be provided in response to a user input when the imaging modality 456 acquires the image data 472.

In some examples, as disclosed herein the 3D image data may include a model of one or more anatomical structures, such as in the form of a 3D mesh corresponding to a surface of a vessel. A 3D projection matrix (e.g., perspective or parallel projection matrix) may be applied to the mesh that was generated from the pre-operative image 480, such as disclosed herein. If the angle of the C-arm is known for each of the intraoperative images, one 3D projection of the mesh is performed to match the angle for each intraoperative image. If the angle of the C-arm is not known, multiple 3D projections may be generated along different angles, and there may be a manual or automated selection of a "best fit" match between the respective 3D projections and the respective two-dimensional image.

A point generator 484 is programmed to generate spatial points in each of the 2D images (provided by image data 472) and the corresponding projections of the 3D image (provided by projection calculator 482). Rather than working with spheres or corners of markers, the points are selected as features that are visible in both 2D image data 472 and the 3D image data 480. In other examples, the intraoperative image data 472 may be acquired as 3D data, such as acquired by a cone-beam CT or other intraoperative 3D imaging modality. In such an example, the projection calculator may be omitted to enable point generator 484 to identify and generate respective sets of points in 3D space provided by both image data sets 472 and 480.

As a further example, the features include structures such as bony landmarks on the spine, bits of calcification that are visible in both types of images, or points on vessels in an example when contrast is used in both images. Other feature or fiducial points may be used in other examples. In some examples, a common set of features may be located in an automated method (e.g., feature extraction). Additionally or alternatively, one or more such features may be selected in response to a user input provided through a user interface 486, such as graphical user interface interacting with the respective images and projections provided to the point generator. For instance, a user may see a common visible structure among the different views and select/tag it (e.g., through a mouse, keyboard, gesture or other input) in each view. The point generator 484 thus generates points for each predetermined feature and/or user selected feature. The point generator thus operates similarly to the marker point generator 476, just using a different set of landmarks. Since the image data 480 are in 3D, in some examples, the user can identify selected points (through user interface 486) using a set of orthogonal views (e.g., axial, coronal, and sagittal views) of the 3D images of image data 480 to directly measure the x, y, and z locations in the 3D coordinate system of the image data 480. In examples where the intraoperative image data is in 2D space, each of these locations may be converted to two-dimensional coordinates and provided as such in the forward projections provided by the projection calculator 482. The point generator 484 is programmed to locate the same points in the 2D image data, such as by using a vector-crossing function applied to the 2D images, such as the closest point function disclosed herein. In other examples where the intraoperative image data is in 3D space, the point generator 484 can locate the points in 3D coordinates of both image sets, such as automatically or assisted by a user input through the user interface 486.

The resulting points in the respective images are provided to a second transform calculator 488 for generating the transform matrix 414. The transform calculator 488 is programmed to compute the transform matrix to align the images of the image data 472 with the 3D image data 480 based on the common points provided by the point generator 484. For example, the transform calculator 488 constructs the transform matrix (T2) 414 by implementing an error minimization function with respect to the common set of points, such as single value decomposition described with respect to the first transform calculator 478. Other error minimization functions may be used in other examples.

In some examples, the system 400 includes a transform correction function 490 programmed to implement manual corrections to one or more of the transform matrices based on instructions provided via a correction user interface 492. Manual corrections can be applied even if an estimate of the T1 or T2 transform has already been made. For example, if the image data 480 and/or 472 does not have a well-defined set of measured points (e.g., on the spine or other anatomic structure) to work from to perform the registration, the system may define an initial estimate for the transform T2 or, in some examples, an arbitrary T2 transform (e.g. an 'identity' matrix) and allow the user to make corrections through the correction function 490 to generate the final T2 transform 414.

By way of further example, a registration manager 494 is programmed to select and control the application of the respective transform matrices 410, 412 and 414. For example, spatial domains for one or more output visualization space may be set automatically or response to a user input. For each output visualization space, the registration manager can define a set of one or more transforms to apply to enable images and models to be rendered properly in each respective output space. For example, the output spaces may include the AR display, a display of a mobile device or computer. Each display may further include multiple windows (e.g., screen partitions) that can each display a different visualization, including a spatial domain of any of the tracking system, the intraoperative image data, the AR display or the prior 3D image. Thus, registration manager 494 can define a set of transform matrices and apply them to render the correct output image in the desired spatial domain.

Figure 6:
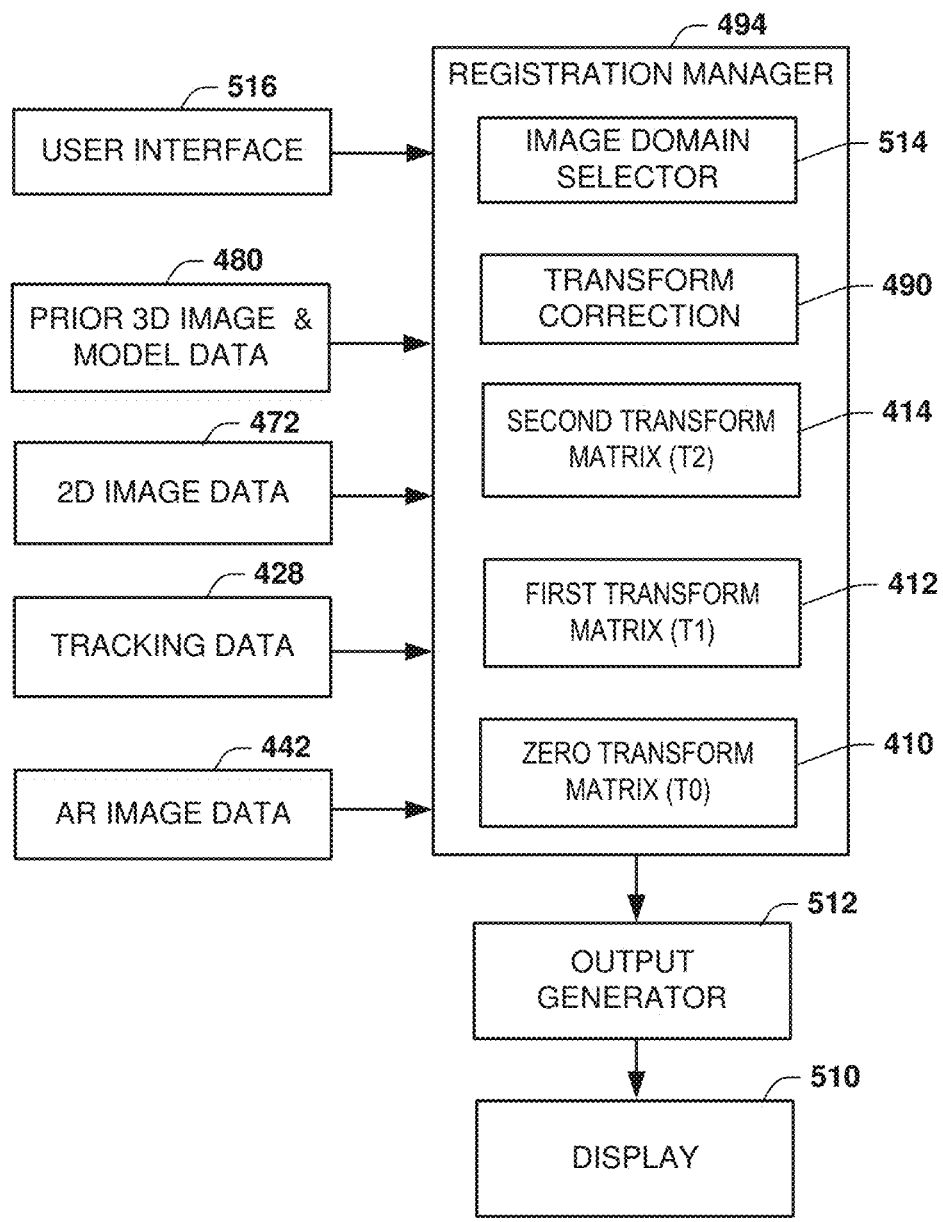
FIG. 6 depicts an example of a registration manager to control use or corrections to one or more affine transformations.

As a further example, with reference to FIG. 6, the registration manager 494 may be used to control application of one or more of the transforms 410, 412 and 414 as well as to control user corrections to one or more of such transforms. The registration manager 494 may be implemented as part of the system 400 of FIG. 5, as shown, or as a separate function. Accordingly, for consistency, functions and data introduced in FIG. 5 are depicted in FIG. 6 using the same reference numbers. Reference may be made back to FIG. 5 and the corresponding description for further information about such functions and data.

The registration manager 494 includes the transform correction function 490 as well as the first and second transform matrices 412 and 414, respectively. In this example, it is assumed that one or both of the transform matrices 412 and 414 may be in need of correction. The need for correction may be made manifest to a user by applying a transform to register two or more domains and provide a resulting visualization on a display 510. For example, an output generator 512 is configured to render a visualization in a selected domain, such as may be the coordinate system of the AR device 440, the coordinate system of the tracking system 424, the coordinate system of the intraoperative image data 472 or the coordinate system of the prior 3D image data 480.

In an example, the manager 494 includes a domain selector 514 programmed to select which domain the output visualization is being rendered based on a user input instruction received via a user interface 520. Additionally, based on the selected domain, the registration manager applies one or more of the transforms T0, T1 or T2 accordingly. As an example, the following table provides a description of which one or more transforms are applied to the image data 472, 480 or tracking data 426 as well as models that may have been generated in a respective coordinate system for each selected domain to which the output visualization is being rendered by the output generator 512. The registration manager 494 further may be used to control the application of the respective transforms to provide a visualization in a selected domain, such as by applying one or more transforms or inverses of such transforms through matrix multiplication, such as set forth in the table.

their respective locations in the 3D image, correction may be needed to T2. A user thus can adjust the alignment of the 2D image with respect to the 3D image (or the forward projection thereof) through the user interface 516. As mentioned, the adjustments may include translation in two dimensions, rotation and/or scaling in response to instructions entered through the user interface using an input device (e.g., mouse or keyboard). The output generator 512 may update the visualization shown in the display to show the image registration in response each adjustment (e.g., in real time). Once a desired alignment is visualized, the user can employ the user interface 516 to apply and store the corrections to the transform T2, and an updated T2 may be stored in memory for subsequent applications. Similar types of adjustments may be made with respect to the first transform matrix 412.

Figure 7:
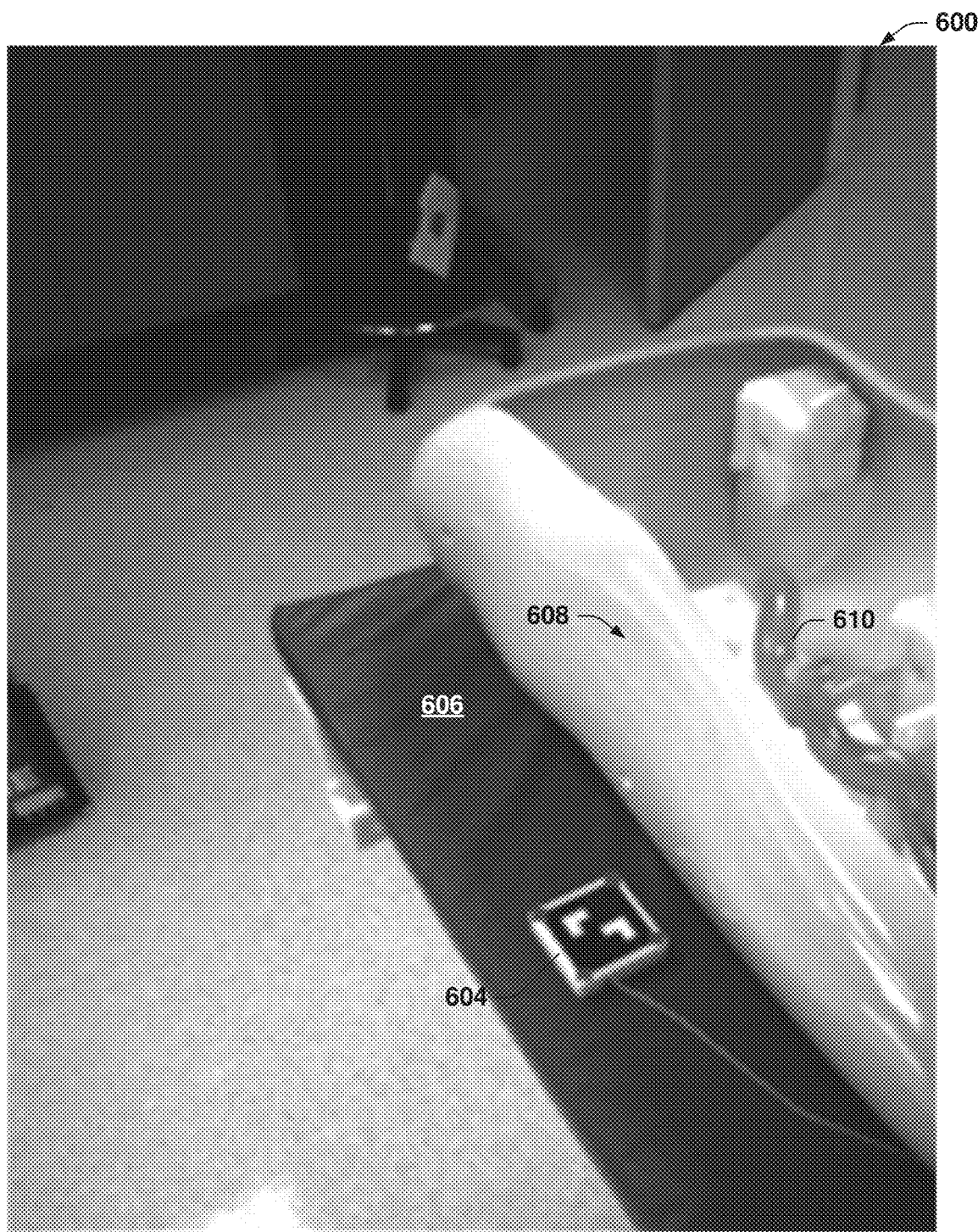
FIGS. 7 and 8 are images from respective cameras of an augmented reality device that includes a multi-modal marker adjacent a co-registered model of an anatomic structure.
Figure 8:
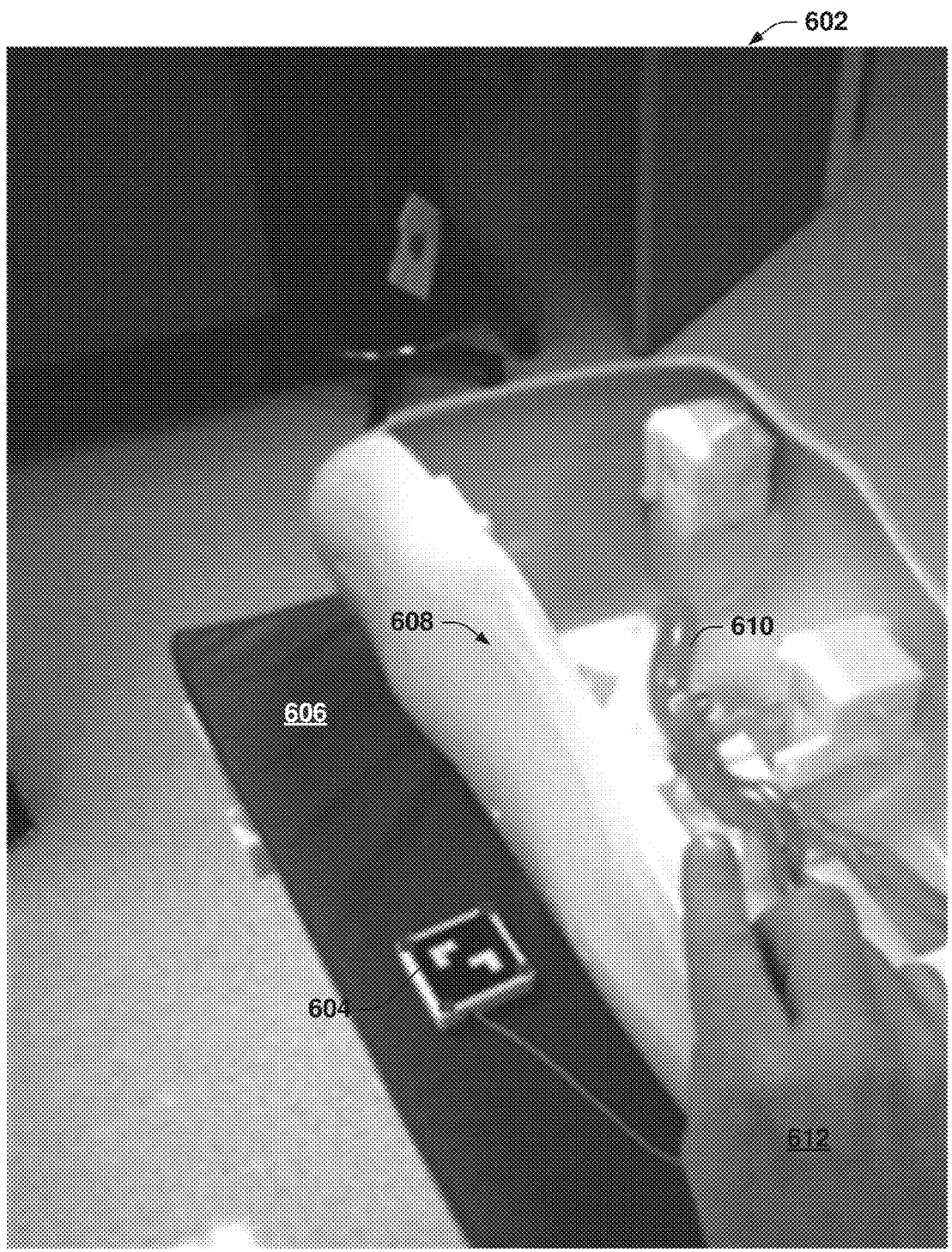

FIGS. 7 and 8 depict examples of images 600 and 602 acquired from respective forward-facing cameras of an AR head set. In this example, a multi-modal marker (e.g., corresponding marker 250, 302) 604 is positioned on a table 606 adjacent to a physical model of patient's body 608

|                     | AR        | Tracking    | Medical Imaging | Prior 3D               |
|---------------------|-----------|-------------|-----------------|------------------------|
| to AR:              | [identity]| inv(T0)     | inv(T0)*inv(T1) | inv(T0)*inv(T1)*inv(T2)|
| to Tracking:        | T0        | [identity]  | inv(T1)         | inv(T1)*inv(T2)        |
| to Medical Imaging :| T1*T0     | T1          | [identity]      | inv(T2)                |
| to Prior 3D:        | T2*T1*T0  | T2*T1       | T2              | [identity]             |

As a further example, manual corrections to either transform 412 or 414 can be provided by multiplying the respective transform matrix T0, T1 or T2 by a correction matrix, such as follows:
  correctedT0=mult(correctionMatrix, T0),
  correctedT1=mult(correctionMatrix, T1) or
  correctedT2=mult(correctionMatrix, T2)
In an example, the supported types of corrections include translation, rotation and scaling, such as may be applied in the form of matrices, as follows:

$$translationMatrix = [1, 0, 0, translation.x, 0,$$
$$1, 0, translation.y, 0, 0, 1, translation.z, 0, 0, 0, 1]$$
$$scalingMatrix = [scale, 0, 0, 0, 0, scale, 0, 0, 0, 0, scale, 0, 0, 0, 0, 1]$$
$$rotationMatrix = (\text{depends on axis of rotation})$$

By way of further example, a user initiates corrections using mouse-down/drag/mouse-up actions or other actions through the user interface 516. The values used in the correction matrix may be set based on the projection matrix used to display the viewport on the display 510. For example, a translation initiated from an AP view would result in the X and Y mouse movements being used to set translation.x and translation.z values (translation.y would be 0). Such transformations thus allow the user to change the view of a single image or the alignment of multiple images.

As a further example, such as when implementing corrections for transform T2, the domain registration manager 494 applies the transform T2 to the image data 472 and the output generator 512 provides a visualization of the 2D images registered in the 3D image based on the transform T2. If the landmarks are properly aligned, as shown on the display 510, no correction may be needed. However, if the locations of landmarks in the 2D image do not align with containing simulated organs 610. In a real person, it is understood that organs within the body would not be visible, but are shown to help demonstrate the accuracy of the transforms generated based on the systems and methods disclosed herein. In FIG. 8, the image 602 is from a slightly different viewing angle and includes the AR marker 604 and a hand 612 of a user (e.g., the individual using the AR device).

As shown in the images 600 and 602, the marker 604 includes portions (e.g., corners) that are identified (e.g., by functions 444 and 446) in the coordinates system of the AR display. The same points of the marker 604 are located in the tracking coordinate system based on sensor data generated by a marker tracking sensor (e.g., sensor 434) to enable a time-varying transform matrix (e.g., matrix 410) to be generated, as disclosed herein. Other transform matrices (e.g., matrices 412 and 414) further may be generated as disclosed herein to align other coordinate systems as well as images and/or models that may have been generated in such other coordinate systems.

Figure 9:
FIG. 9 depicts an example of an augmented reality visualization generated based on registration performed according to the method of FIG. 1.

FIG. 9 depicts an AR image 650 similar to FIGS. 7 and 8 including a holographic overlay of a mesh model 652 superimposed on the simulated organs 610). The same reference numbers used in FIGS. 7 and 8 are also used in FIG. 9 to show similar parts. The overlay is aligned with the patient's anatomy (organs 610) in the AR display image 650 based on applying a set of transforms to the mesh model 652 (e.g., according to the method 100 of FIG. 1 and system 400). For example, where the mesh model 652 is generated in the coordinate system of the 3D prior image, the model may be co-registered in the AR coordinate system by applying the inverses of each of the transforms T0, T1 and T2 to the mesh model (e.g., inv(T0)*inv(T1)*inv(T2), such as shown in the table herein).

In some examples, annotations 654 are shown in the output visualization to provide the user with additional information, such as distance from an object (e.g., to which an object tracking sensor 438 is attached) to a target site and a projected angle. The view further may be modified (e.g., enhanced) in response to a user input (e.g., on a user input device, voice commands or gesture commands). For example, the output engine that generates the holographic visualization on the AR display may zoom or magnify a current view that is overlayed on the patient's body—in a real visual field. Additionally or alternatively, a user may enter commands to change the viewing angle. In some examples, such as when enabled, the corners of the marker 604 (or other portions thereof) may be illuminated or otherwise differentiated in the output visualization to confirm that such portions of the marker are properly registered. Other image enhancements are also possible.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in one or more non-transitory machine-readable media), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:
   acquiring images from cameras, each having a known position and orientation with respect to a spatial coordinate system of an augmented reality device, the acquired images including predetermined portions of a multi-modal marker device that have a fixed known spatial position with respect to at least one tracking sensor of the multi-modal marker device, the at least one tracking sensor having a three-dimensional position that is detectable in a coordinate system of a tracking system, wherein the multi-modal marker device includes a fiducial marker having a rectangular-shaped border and respective corners where edges thereof meet, which is visible in at least some images acquired by the cameras, the fiducial marker being identified in the images that are acquired by the cameras and coordinates of the predetermined portions of the multi-modal marker device being determined for each identified fiducial marker;
   estimating a three-dimensional position for the predetermined portions of the multi-modal marker device with respect to the spatial coordinate system of the augmented reality device based on each of the respective acquired images and the known position and orientation of the cameras with respect to the spatial coordinate system of the augmented reality device; and
   computing an affine transform configured to register the coordinate system of the tracking system with a visual space of a display that is in the spatial coordinate system of the augmented reality device based on the estimated three-dimensional position for respective predetermined portions of the multi-modal marker device and the known spatial position of the predetermined portions of the multi-modal marker device relative to the at least one tracking sensor.

2. The method of claim 1, wherein the affine transform is a given affine transform, the method further comprising determining at least one other affine transform for registering a three-dimensional coordinate system of a model space with the coordinate system of the tracking system.

3. The method of claim 2, wherein anatomical model data is stored in memory to represent at least one three-dimensional model of patient anatomy for an internal anatomical structure in the model space, the method further comprising:
   applying the given affine transform and the other affine transform to the anatomical model data to map the at least one three-dimensional model of patient anatomy for the internal anatomical structure into the visual space of the display that is in the spatial coordinate system of the augmented reality device.

4. The method of claim 3, wherein the at least one three-dimensional model of patient anatomy for the internal anatomical structure comprises a mesh structure derived in the model space based on three-dimensional prior image data acquired by a pre-operative medical imaging modality.

5. The method of claim 2, wherein the model space comprises a three-dimensional spatial coordinate system of a prior three-dimensional pre-operative medical imaging modality, and wherein determining the other affine transform, further comprises:

computing a first transform for registering a coordinate system of an intraoperative medical imaging modality with a coordinate system of a three-dimensional medical imaging modality that defines the model space; and
computing a second affine transform for registering a three-dimensional coordinate system of the tracking system with the three-dimensional coordinate system of the intraoperative medical imaging modality based on the estimated position for the respective predetermined portions of the multi-modal marker device and a known relationship of the at least one tracking sensor and the respective predetermined portions of the multi-modal marker device.

6. The method of claim 1, further comprising applying the affine transform to tracking data acquired by the tracking system for the at least one tracking sensor to map a position and orientation of the at least one tracking sensor into the visual space of the display that is in the spatial coordinate system of the augmented reality device.

7. The method of claim 1, wherein coordinates of each of the predetermined portions of the multi-modal marker device are determined based on locations of pixels the predetermined portions in each of the respective acquired images.

8. The method of claim 7,
wherein the predetermined portions of the marker correspond to the respective corners of the border.

9. The method of claim 1, wherein the cameras are at known positions with respect to the display of the augmented reality device and configured to acquire the images to include non-parallel images with an overlapping field of view.

10. The method of claim 9, wherein the augmented reality device includes a headset that includes the cameras and the display thereof, the display being a head-mounted display configured to overlay a holographic image on the display within a user's field of view.

11. The method of claim 9, wherein the augmented reality device includes a smart phone or tablet computer.

12. The method of claim 1, wherein computing the affine transform is repeatedly performed on images frames that are acquired by the cameras to update the affine transform to accommodate for movement of the cameras relative to the predetermined portions of the multi-modal marker device.

13. One or more non-transitory computer-readable media programmed to perform the method of claim 1.

14. A system comprising:
an augmented reality device that includes cameras to acquire images for respective fields of view;
one or more non-transitory computer-readable media to store data and instructions executable by a processor, the data comprising:
augmented reality image data for images acquired by the cameras, each camera having a known position and orientation with respect to a spatial coordinate system of the augmented reality device, the augmented reality image data including predetermined portions of a multi-modal marker device having a fixed known spatial position with respect to at least one tracking sensor of the multi-modal marker device, wherein the multi-modal marker device includes a fiducial marker that is visible in at least some of the images acquired by the cameras, the fiducial marker including a rectangular-shaped border having respective corners where edges thereof meet, the at least one tracking sensor having a three-dimensional position that is detectable in a coordinate system of a tracking system;
the instructions comprising:
code to identify the fiducial marker in at least some of the images acquired by the cameras; positions of the predetermined portions of the multi-modal marker device are determined for each identified fiducial marker
code to generate a three-dimensional position for the predetermined portions of the multi-modal marker device for each identified fiducial marker with respect to the spatial coordinate system of the augmented reality device based on the augmented reality image data that is acquired and the known position and orientation of the cameras with respect to the spatial coordinate system of the augmented reality device; and
code to compute an affine transform for registering the coordinate system of the tracking system with a visual space of a display that is in the spatial coordinate system of the augmented reality device based on the three-dimensional position for the respective predetermined portions of the multi-modal marker device and the known spatial position and orientation of the predetermined portions of the multi-modal marker device relative to the at least one tracking sensor.

15. The system of claim 14, wherein the affine transform is a given affine transform, the instructions further comprising code to compute at least one other affine transform for registering a three-dimensional coordinate system of a model space with the coordinate system of the tracking system.

16. The system of any of claim 15, wherein the data further comprises anatomical model data stored to represent at least one three-dimensional model of patient anatomy for an internal anatomical structure in the model space, the instructions further comprising:
code to apply the given affine transform and the other affine transform to the anatomical model data to co-register the at least one three-dimensional model of patient anatomy for the internal anatomical structure in the visual space of the display that is in the spatial coordinate system of the augmented reality device.

17. The system of claim 16, wherein the at least one three-dimensional model of patient anatomy for the internal anatomical structure comprises a mesh structure derived in the model space based on three-dimensional prior image data acquired by a pre-operative medical imaging modality.

18. The system of claim 15, wherein the code to compute the other affine transform further comprises:
code to compute a first transform for registering a coordinate system of an intraoperative medical imaging modality with a coordinate system of a three-dimensional medical imaging modality that defines the model space; and
code to compute a second affine transform for registering a three-dimensional coordinate system of the tracking system with the three-dimensional coordinate system of the medical imaging modality based on estimated positions for the respective predetermined portions of the multi-modal marker device and a known relationship of the at least one tracking sensor and the respective predetermined portions of the multi-modal marker device.

19. The system of claim 14, further comprising the tracking system that is configured to provide sensor tracking data indicative of a position and orientation of the at least one tracking sensor, wherein the instructions further comprise code to apply the affine transform to the sensor tracking data to map a position and orientation of the at least one tracking sensor into the visual space of the display that is in the spatial coordinate system of the augmented reality device.

20. The system of claim 14, wherein the code to generate the three-dimensional position of each of the predetermined portions of the multi-modal marker device is further programmed to determine the three-dimensional position of each of the predetermined portions of the multi-modal marker device based on locations of pixels the predetermined portions in each of the respective acquired images acquired by the cameras.

21. The system of claim 20, wherein the predetermined portions of the marker correspond to the respective corners of the border.

22. The system of claim 14, wherein the cameras are at known positions with respect to the display of the augmented reality device and configured to acquire the images as non-parallel images having an overlapping field of view.

23. The system of claim 22, wherein the augmented reality device includes a headset that includes the cameras and the display thereof, the display being a head-mounted display configured to overlay a holographic image on the display within a user's field of view.

24. The system of claim 22, wherein the augmented reality device includes a smart phone or tablet computer.

25. The system of claim 14, wherein the code to compute the affine transform is programmed to repeatedly compute the affine transform on images frames that are acquired by the cameras to update the affine transform to accommodate for movement of the cameras relative to the predetermined portions of the multi-modal marker device.

\* \* \* \* \*